(12) United States Patent
Sun et al.

(10) Patent No.: US 8,180,101 B2
(45) Date of Patent: May 15, 2012

(54) CALIBRATION METHOD FOR STRUCTURE PARAMETERS OF STRUCTURED-LIGHT VISION SENSOR

(75) Inventors: Junhua Sun, Beijing (CN); Guangjun Zhang, Beijing (CN); Zhenzhong Wei, Beijing (CN)

(73) Assignee: Beihang University, Beijing (CN)

( * ) Notice: Subject to any disclaimer, the term of this patent is extended or adjusted under 35 U.S.C. 154(b) by 1142 days.

(21) Appl. No.: 12/022,681

(22) Filed: Jan. 30, 2008

(65) Prior Publication Data

US 2009/0059011 A1  Mar. 5, 2009

(30) Foreign Application Priority Data

Sep. 5, 2007 (CN) ............ 2007 1 0121397

(51) Int. Cl.
*G06K 9/00* (2006.01)
*H04N 17/00* (2006.01)
(52) U.S. Cl. .................... 382/100; 348/180
(58) Field of Classification Search .............. None
See application file for complete search history.

(56) References Cited

U.S. PATENT DOCUMENTS

| | | | | |
|---|---|---|---|---|
| 4,463,380 A * | 7/1984 | Hooks, Jr. | ............ | 348/580 |
| 5,155,775 A * | 10/1992 | Brown | ............ | 382/153 |
| 5,531,520 A * | 7/1996 | Grimson et al. | ............ | 382/131 |
| 6,064,759 A * | 5/2000 | Buckley et al. | ............ | 382/154 |
| 6,064,760 A * | 5/2000 | Brown | ............ | 382/154 |
| 6,219,063 B1 * | 4/2001 | Bouguet et al. | ............ | 345/426 |
| 6,600,168 B1 * | 7/2003 | Geng | ............ | 250/559.22 |
| 6,621,921 B1 * | 9/2003 | Matsugu et al. | ............ | 382/154 |
| 6,781,618 B2 * | 8/2004 | Beardsley | ............ | 348/43 |
| 6,917,702 B2 * | 7/2005 | Beardsley | ............ | 382/154 |
| 6,980,690 B1 * | 12/2005 | Taylor et al. | ............ | 382/154 |
| 7,003,136 B1 * | 2/2006 | Harville | ............ | 382/103 |
| 7,106,898 B2 * | 9/2006 | Bouguet et al. | ............ | 382/154 |
| 7,242,818 B2 * | 7/2007 | Beardsley et al. | ............ | 382/291 |
| 7,277,599 B2 * | 10/2007 | Eian et al. | ............ | 382/285 |
| 7,306,337 B2 * | 12/2007 | Ji et al. | ............ | 351/209 |
| 7,324,686 B2 * | 1/2008 | Nister | ............ | 382/154 |

* cited by examiner

*Primary Examiner* — Manav Seth
(74) *Attorney, Agent, or Firm* — Workman Nydegger

(57) ABSTRACT

This disclosure provides a calibration method for structure parameters of a structured-light vision sensor, which includes setting up the coordinate frames of a camera, image plane and target for calibration. The calculation of coordinates in the camera coordinate frame of stripes, projected by structured-light, on the planar target and a structured-light equation fitting according to the coordinates in the camera coordinate frame of the stripes on the planar target, by moving the planar target arbitrarily multiple times. The calibration method of the structured-light vision sensor provided by the disclosure is easy to operate and no auxiliary apparatus is needed, which can not only promote the efficiency of the calibration of structured-light, but also extend the application scope of calibration of structured-light.

16 Claims, 4 Drawing Sheets

CALIBRATION METHOD FOR STRUCTURE PARAMETERS OF STRUCTURED-LIGHT VISION SENSOR

CROSS-REFERENCE TO RELATED APPLICATIONS

This application claims priority from Chinese Patent Application Serial No, 200710121397.X filed Sep. 5, 2007, the disclosure of which, including the specification, drawings and claims, is incorporated herein by reference in its entirety.

TECHNICAL FIELD

This disclosure relates to structured-light vision measurement technology, and more particularly, to a calibration method for structure parameters of structured-light vision sensor.

BACKGROUND

Structured-light vision measurement is a measurement method based in taking images of measurement points or light stripes, which is formed by the intersection of a structured-light projected by a laser and the surface of an object being measured, by a camera, and then acquiring 3D information regarding the object surface using a laser triangular principle. According to a mode of laser projection, structured-light vision measurement may be divided into point structured-light, single line structured-light, multiple lines structured-light and circle structured-light, etc. Structured-light vision measurement has the advantage of a large scale of measurement, noncontact, high speed, good system flexibility and moderate precision, which is widely used in the areas of reverse engineering and products online testing, etc.

The key to successful application of structured-light vision measurement is the calibration of structured-light vision sensor, which comprises calibration of the camera's intrinsic parameters and structure parameters, wherein the calibration method of the camera's intrinsic parameters is not introduced here because it is relatively mature. So far, as to the calibration for the structure parameters of the structured-light vision sensor, many scholars have researched the subject and presented some new methods such as a fiber drawing method, sawtooth target method and a cross ratio invariability method based on the 3D target, etc.

To be more specific, the so called "fiber drawing method" lets the structured-light project on some spatial distributed fibers which are non-coplanar. Because of the dispersion of the fibers, bright points are formed on the fibers and imaged on the image plane. The spatial coordinates of the bright points may be measured by electronic theodolite, thereby permitting solving of the position parameters between the structured-light and the camera by the bright points' coordinates in the image plane and spatial. This calibration method needs two electronic theodolites to measure the spatial coordinates of the bright points. If more calibration points are acquired, multiple times of manual aim are needed, of which the operations are complicated.

When it comes to the sawtooth target method, an article entitled "A New Structure Parameters Calibration Method of Structured-light Vision Sensor" and published in the Chinese Journal of Scientific Instrument, 2000, 21(1):108-110 by Fajie Duan et al. presents a structure parameters calibration method of a structured-light vision sensor according to the features of structured-light vision sensor, in which a simple calibration target and a 1D bench are used to realize the highly precise calibration of a line structured-light sensor. In this method, no other auxiliary apparatus is needed to measure the coordinates of the points on the light plane. However, the operations of the method are complicated because the attitude of the 1D bench or the structured-light sensor should be adjusted in order to make the light plane perpendicular to the edge line. Moreover, the cost of processing a sawtooth target is high, while the sawtooth edge line is limited and the calibration points that can be acquired are less.

Concerning the cross ratio invariability method based on a planar target, it is a calibration method for the structure parameters of a structured-light vision sensor. The cross ratio invariablilty method is described in an article entitled "Complete Calibration of a Structured-light Stripe Vision Sensor Through Planar Target of Unknown Orientations[J], Image and Vision Computing, Volume 23, Issue 1, January 2005, Pages 59-67)" by Fuqiang Zhou. This method uses the cross ratio invariability principle to acquire a calibration point, the lines of which on the target are few, usually 3 to 10 lines. Only one calibration point can be found in a line of feature points (at least three). Therefore, using this method, 3 to 10 calibration points from the target at one position may be obtained. This method requires no auxiliary apparatus, and there is no occlusion problem and the operations are simple. That is why the method is only suitable for line structured-light calibration, and there will be a large fitting error when the method is used to calibrate non-line structured-light.

As to the rapid calibration method of the line structured-light sensor based on a coplane reference, this calibration method is for the structure parameters of a structured-light vision sensor, as described in a Chinese patent by Jigui Zhu, entitled, "Rapid Calibration Method of Line Structured-light Sensor Based on Coplane Reference", the patent number of which is 200510013231.7. The method calibrates a line structured-light based on an intersection line of the coplane reference and the plane determined by the optical center of the camera and the images of the line light stripes. This method requires no auxiliary apparatus, and there is no occlusion problem and the operations are simple, whereas, it can only be used in the calibration of a line structured-light or a multiple lines structured-light.

According to the analysis above, the fiber drawing method requires electronic theodolites as an auxiliary apparatus and multiple times of manual aim which is complicated to operate. A few calibration points may be acquired in the sawtooth target method because the sawtooth edges are limited, but the cost of processing the sawtooth target is high. The scope of the calibration method of cross ratio invariability based on planar target and rapid calibration method based on coplane reference for line structured-light sensor is small. The two methods are only suitable for calibration of line structured-light or multiple lines structured-light.

SUMMARY

Accordingly, one focus of this disclosure is to present a calibration method for the structure parameters of a structured-light vision sensor, which can provide high efficiency of structured-light calibration simple operation without requiring an auxiliary apparatus, and extent the application scope of the calibration of structured-light.

The technical scheme of an embodiment of the disclosure is described as follows.

A calibration method for the structure parameters of a structured-light vision sensor comprises the following steps:

A. setting up coordinate frames of a camera and an image plane;

B. setting up a target coordinate frame, acquiring images of a planar target which is used to calibrate structure parameters of the sensor, and finding coordinates in the camera coordinate frame of stripes projected by structured-light on the planar target; and C. acquiring the coordinates in the camera coordinate frame of the stripes projected by the structured-light on the target plane multiple times and fitting a structured-light equation according to all the coordinates of light stripes acquired.

In the schemes above, the structured-light in step C may be a structured-light of any pattern.

In step C above, in one embodiment, acquiring the coordinates of the light stripes projected on the target plane multiple times includes moving the planar target arbitrarily multiple times, and repeating step B each time the planar target is moved.

In another embodiment, before step B above, the planar target is placed with feature points arbitrarily in the measurement area of the structured-light vision sensor, and bright light stripes are formed on the planar target by the projection of the structured-light.

In step B above, acquiring the images of the planar target used to calibrate the sensor's structure parameters may further comprise: taking images of the planar target with the camera and correcting distortion on the images of the planar target, wherein the images of planar target includes light strips and at least four non-collinear feature points.

In step B above, acquiring the coordinates in the camera coordinate frame of the stripes projected by the structured-light on the planar target comprises:

b1. extracting the coordinates of feature points on the images of the planar target used to calibrate the structure parameters of the sensor;

b2. solving a homographic matrix between the image plane and the target plane, and a rotation matrix and translation vector from the target coordinate frame to the camera coordinate frame according to the feature points extracted;

b3. extracting the coordinates of the light stripes on the images of the planar target used to calibrate the structure parameters of the sensor, solving the coordinates in the target coordinate frame of the light stripes on the target according to a transformation between the image plane and the target plane, and converting the coordinates into the camera coordinate frame according to the transformation from the target coordinate frame to the camera coordinate frame.

The calibration method for the structure parameters of a structured-light vision sensor presented in the disclosure, in which the position of the planar target is moved arbitrarily multiple times and the coordinates of the light stripes are calibrated only by four or more non-collinear feature points on the target images, can provide high efficiency of a structured-light calibration, simple operation without requiring an auxiliary apparatus to acquire coordinates of calibration points. The structured-light projected from the laser projector can be any pattern of structured-light, so that the implementation is more flexible and diverse, and the application scope of the calibration of structured-light can be extended.

BRIEF DESCRIPTION OF THE DRAWINGS

The accompanying drawings, which are incorporated in and constitute a part of specification, illustrate an exemplary embodiment of the present disclosure and, together with the general description given above and the detailed description of the preferred embodiment given below, serve to explain the principles of the present disclosure.

DETAILED DESCRIPTION

Figure 1:
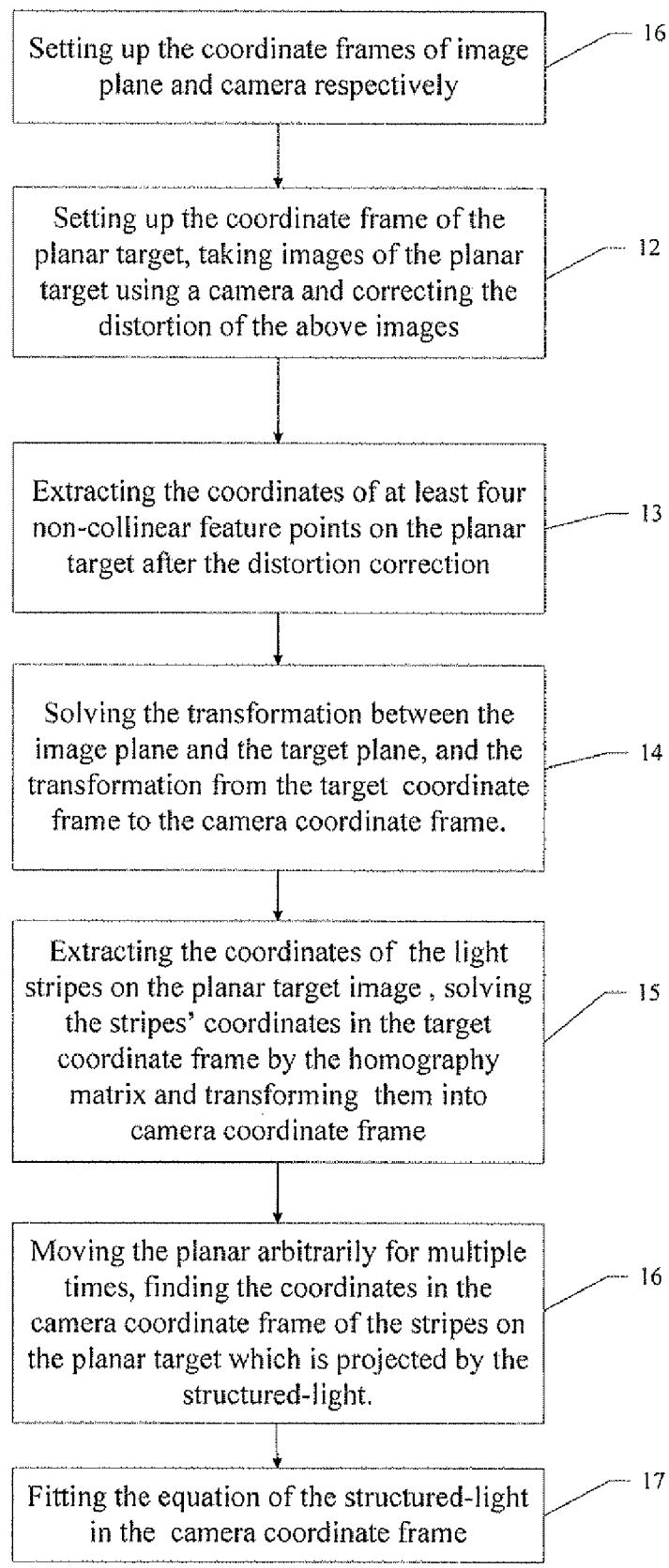
FIG. 1 illustrates the flow diagram of an exemplary calibration method for structure parameters of a structured-light vision sensor.

While the claims are not limited to the illustrated embodiments, an appreciation of various aspects of the present disclosure is best gained through a discussion of various examples thereof. Referring now to the drawings, illustrative embodiments will be described in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description.

FIG. 1 illustrates a flow diagram of a calibration method for structure parameters of a structured-light vision sensor according to an embodiment of this disclosure. As shown in FIG. 1, the calibration method disclosed herein comprises the following steps.

Figure 2:
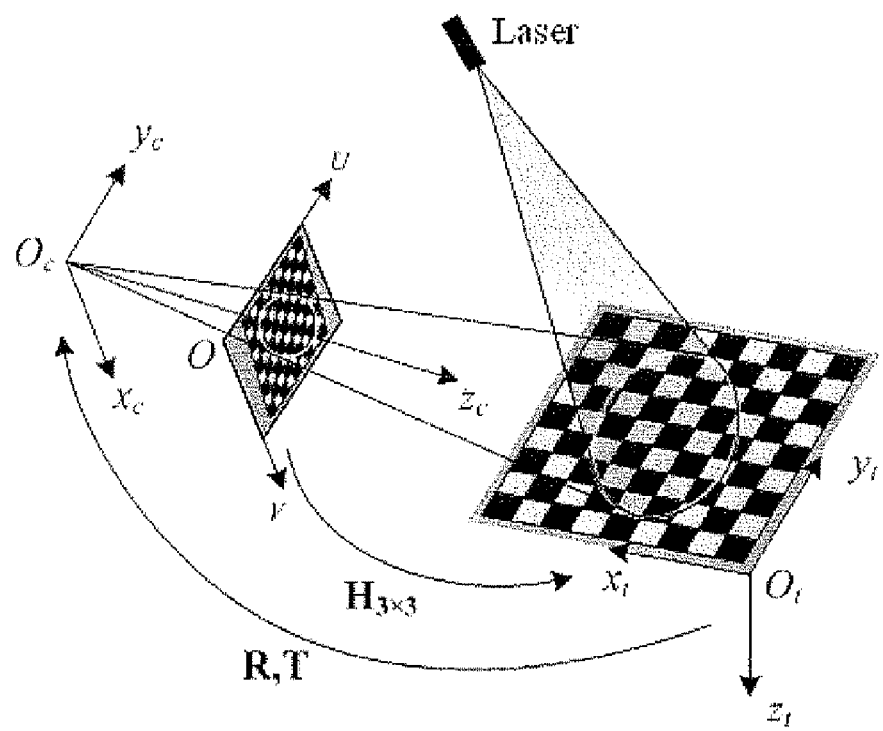
FIG. 2 illustrates a schematic representation of the calibration method.

1) First, coordinate frames of an image plane and camera are set up, respectively. As shown in FIG. 2, $O_c$-$x_c y_c z_c$ and O-UV are the coordinate frames of the camera and the image plane respectively, which are set up according to the position of the camera.

Figure 3:
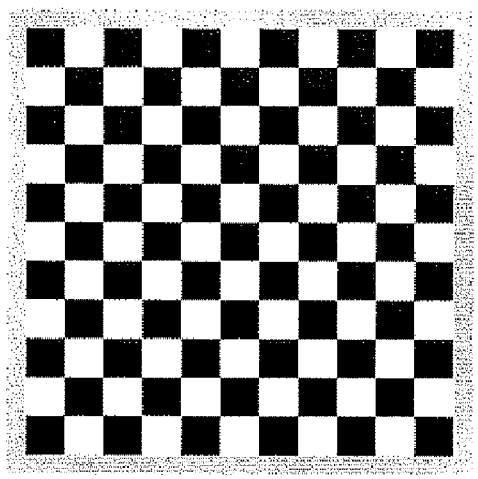
FIG. 3 is a plan view of a planar target.

2) Next, the target coordinate frame is set up, taking the images of the planar target using the camera and correcting any distortion of the above images. The planar target with feature points is placed arbitrarily in the measuring range of the structured-light sensor. When the laser projector operates, it projects a pattern of light stripes on the planar target. Here, the planar target is set in advance. As shown in FIG. 3, the set target is a 2D plane with square markers thereon. The corners of the squares are used as feature points. The numbers of the feature points could range from about 4 to 200. In one embodiment, the length of the squares sides are from about 3 mm to 50 mm, and the tolerance of the lengths of each side are from about 0.001 mm to 0.011 mm.

As shown in FIG. 2, the target coordinate frame is set up according to the position of the planar target, which is defined as $O_t$-$x_t y_t z_t$.

The image of the planar target should include the light stripes generated by the projector and at least four non-collinear feature points. The distortion correction mentioned above utilizes the intrinsic parameters of the camera to correct the distorted image of the planar target. The distortion correction method has been studied in depth by prior researches, and will not be discussed here.

3) Next, the coordinates of at least four non-collinear feature points on the planar target image is extracted after the distortion correction is conducted in step 2.

In the present embodiment, the pixel-precision coordinates of the corner points are determined using a shape operator based on the Hessian matrix, then the gray level distribution of the neighborhood of the feature points is described by the second order Taylor expansion, and finally the sub-pixel coordinates of the feature point is solved by calculating a saddle point of the curved surface.

Detailed implementation of the sub-pixel detector is explained in Dazhi Chen's article, entitled, "A New Sub-Pixel Detector for X-Corners in Camera Calibration Targets[C], WSCG'2005 Short Papers Proceedings, 13$^{th}$ International Conference in Central Europe on Computer Graphics, Visualization and Computer Vision, 2005, Plzen, Czech Republic," the disclosure of which is incorporated herein by reference.

4) Next, the transformation between the image plane and the target plane is solved, and transformation from the target coordinate frame to the camera coordinate frame using the coordinates of the feature points extracted in step 3.

The transformation between the image plane and target plane, as mentioned above, refers to the homographic matrix between the two planes, denoted by a 3×3 matrix H, and the transformation from the target coordinate frame to the camera coordinate frame refers to the coordinate transformation denoted by a 3×3 rotation matrix R and a three-dimensional translation vector T.

Typically a linear solution of 3×3 homographic matrix H between the two planes is solved utilizing the least square method, which requires the image coordinates and the corresponding coordinates in $O_t$-$x_t y_t z_t$ of at least four non-collinear feature points. Then, the optimal homographic matrix H is acquired by using the Levenberg-Marquardt nonlinear optimization. Finally, the rotation matrix R and the translation vector T from $O_t$-$x_t y_t z_t$ to $O_c$-$x_c y_c z_c$ are computed by decomposing H.

Details of algorithms for computing the homographic matrix H, rotation matrix R and the translation vector T have been discussed in Z. Y. Zhang's article entitled "A Flexible New Technique for Camera Calibration[R] (Microsoft Corporation, NSR-TR-98-71, 1998), the contents of which are incorporated herein by reference.

5) The coordinates of the light stripes on the planar target image after the said distortion correction in step 2, is extracted. And the coordinates in the target coordinate frame of the light stripes using the homographic matrix H is solved, finally transforming them into the camera coordinate frame.

In step 5), the normal directions of the light stripes, as well as the second derivative along the direction, are acquired by calculating the image point's Hessian matrix and the vector corresponding to the eigenvalue which is the max absolute value in the Hessian matrix, and the center position of the sub-pixel level light stripes is determined. Details of extracting the light stripes center is discussed in greater detail in Carsten Steger's article, "Unbiased Extraction of Curvilinear Structure from 2D and 3D Images [D](Germany, Technology University Munich, 1998)," the contents of which are incorporated herein by reference. The coordinates of the light stripes in the target coordinate frame are acquired by matrix H, and then they are transformed to the camera coordinate frame $O_c$-$x_c y_c z_c$ by the rotation matrix R and translation vector T gotten in step 4).

6) Next, the planar target is moved arbitrarily multiple times, and steps 2 to 5 are repeated after each movement to acquire the coordinates of the light stripes in the camera coordinate frame $O_c$-$x_c y_c z_c$. Here, the number of times the planar target is moved is not restricted, and the number of movements can be set in advance.

7) Next, the equation of the structured-light in $O_c$-$x_c y_c z_c$ is fitted using the coordinates of the light stripes in $O_c$-$x_c y_c z_c$, which are acquired in steps 5) and 6). Then, the equation is stored for the measuring application.

An application of structured-light sensor is described to explain the calibration method for structure parameters of the present embodiment.

Figure 4:
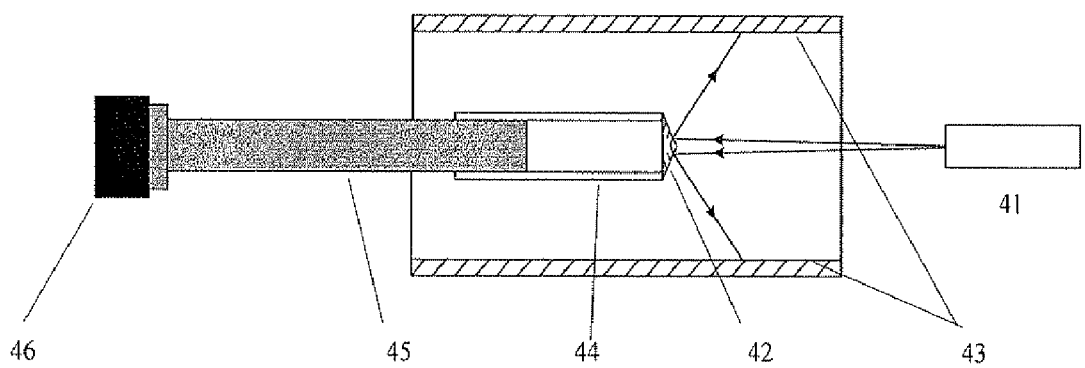
FIG. 4 is a schematic illustration of a structured-light sensor for measuring a 3D shape of an inner surface of a through hole in a microminiature component.

FIG. 4 illustrates a structured-light sensor for measuring a 3D shape of an inner surface of a through hole in a microminiature component. When the sensor works, the conical light beam emitted by the laser 41 is projected to the conical mirror 42. After reflection, it forms a conical structured-light which is projected to the inner surface 43 of the measured object and forms circular light stripes on the surface. The light of the stripes penetrates the glass tube 44 and goes through the endoscope 45. Then the light stripes are imaged by the CCD camera 46. Before using the system, the equation of the conical structured-light should be calibrated.

Figure 6:
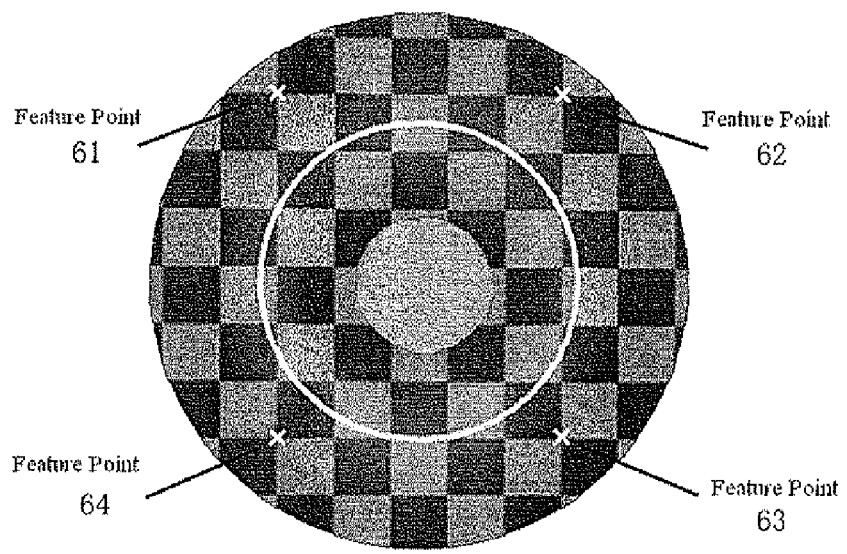
Figure 7:
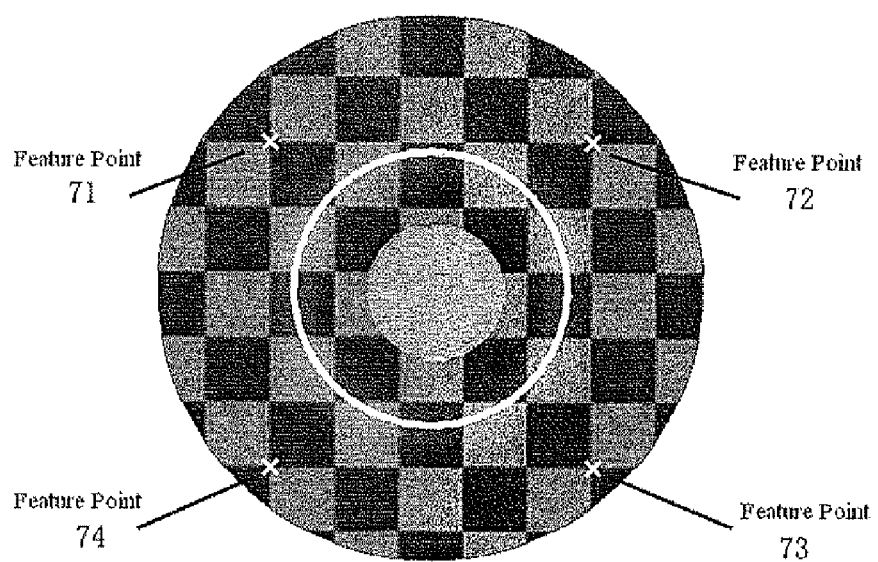

According to the procedure shown in FIG. 1, the equation of the conical structured-light is calibrated using the planar target with a pattern shown in FIG. 2. The target is moved three times arbitrarily, and three images of the target are acquired for calibration, as shown in FIG. 5, FIG. 6, and FIG. 7.

Figure 5:
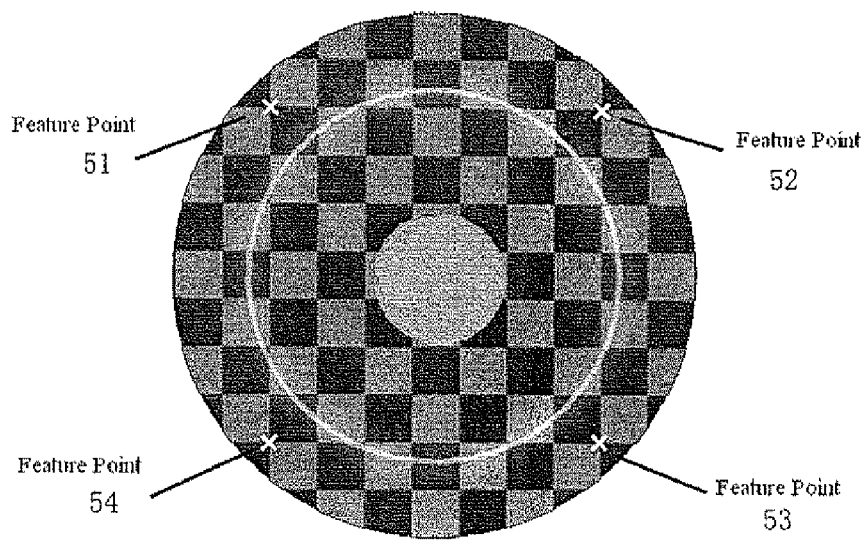
FIGS. 5, 6, and 7 illustrates various views of images of a planar target when placed at three different positions to calibrate a structured-light vision sensor.

The coordinates of the feature points 51, 52, 53 and 54 in FIG. 5 are extracted, which are (119.1, 114.5), (386.3, 115.2), (385.2, 383.4), (119.7, 382.6) respectively, and the corresponding coordinates in the target coordinate frame are (−15, 15), (20, 15), (20, −20), (−15, −20) respectively.

The homographic matrix $H_1$ is computed according to step 4), the rotation matrix $R_1$ and translation vector $T_1$ from the target coordinate frame $O_t$-$x_t y_t z_t$ to the camera coordinate frame $O_c$-$x_c y_c z_c$ are:

$$H_1 = \begin{bmatrix} 7.6104 & -0.0389 & 233.5335 \\ 0.0187 & -7.7101 & 230.1376 \\ 0 & -0.0002 & 1 \end{bmatrix}$$

$$R_1 = \begin{bmatrix} 0.994262 & 0.038286 & 0.099884 \\ 0.045158 & -0.996699 & -0.067475 \\ 0.096971 & 0.071598 & -0.992709 \end{bmatrix}$$

$$T_1 = \begin{bmatrix} 4.233 \\ -4.245 \\ 86.446 \end{bmatrix}$$

The coordinates of the feature points 61, 62, 63 and 64 in FIG. 6 are extracted, which are (140.7, 103.4) (364.3, 105.6), (363.2, 374.9), (141.0, 372.8) respectively, and the corresponding coordinates in the target coordinate frame are (−10, 15), (15, 15), (15, −15), (−10, −15) respectively.

The homographic matrix $H_2$ is computed according to step 4), the rotation matrix $R_2$ and translation vector $T_2$ from the target coordinate frame $O_t$-$x_t y_t z_t$ to the camera coordinate frame $O_c$-$x_c y_c z_c$ are:

$$H_2 = \begin{bmatrix} 8.9194 & -0.0395 & 230.0268 \\ 0.0891 & -9.0287 & 239.3832 \\ 0 & -0.0002 & 1 \end{bmatrix}$$

$$R_2 = \begin{bmatrix} 0.968369 & -0.003242 & 0.249500 \\ 0.009868 & -0.998636 & -0.051277 \\ 0.249326 & 0.052118 & -0.967016 \end{bmatrix}$$

$$T_2 = \begin{bmatrix} 3.526 \\ -3.458 \\ 71.957 \end{bmatrix}$$

The coordinates of the feature points 71, 72, 73 and 74 in FIG. 7 are extracted, which are (127.5, 136.3) (377.4, 138.9), (375.4, 388.1), (127.1, 387.7) respectively, and the corresponding coordinates in the target coordinate frame are (−10, 10), (15, 10), (15, −15) (−10, −15) respectively.

The homographic matrix $H_3$ is computed according to step 4), the rotation matrix R and translation vector T from the target coordinate frame $O_t$-$x_t y_t z_t$ to the camera coordinate frame $O_c$-$x_c y_c z_c$ are:

$$H_3 = \begin{bmatrix} 10.0674 & -0.0170 & 227.5667 \\ 0.1521 & -10.0951 & 237.9409 \\ 0.0004 & -0.0003 & 1 \end{bmatrix}$$

$$R_3 = \begin{bmatrix} 0.999364 & 0.022667 & 0.027530 \\ 0.024393 & -0.997649 & -0.064043 \\ 0.026014 & 0.064674 & -0.997567 \end{bmatrix}$$

$$T_3 = \begin{bmatrix} 2.558 \\ -3.609 \\ 55.349 \end{bmatrix}$$

Finally, the equation of the structured-light fit by the coordinates of the three light stripes in the camera coordinate frame is:

$$x^2 + 1331y^2 + 3z^2 + 80xy + 119yz + 4zx - 218x - 7305y - 324z + 10000 = 0$$

The equation of the structured-light will be employed by the structured-light vision sensor in the measuring process.

The foregoing description of various embodiments of the disclosure has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the disclosure and its practical application to thereby enable one of ordinary skill in the art to utilize the disclosure in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A calibration method for structure parameters of a structured-light vision sensor, comprising the steps of:
    a. setting up coordinate frames of a camera and an image plane;
    b. setting up a target coordinate frame, acquiring images of a planar target which is used to calibrate the structure parameters of the sensor, and finding coordinates in the camera coordinate frame of stripes projected by structured-light on the planar target; and
    c. acquiring coordinates in the camera coordinate frame of the stripes projected by structured-light on the target plane multiple times, and fitting a structured-light equation according to the acquired coordinates.

2. The method according to claim 1, wherein the step of acquiring the stripes coordinates in the target plane multiple times further comprises: moving the planar target arbitrarily multiple times, and repeating step b each time the planar target is moved.

3. The method according to claim 1, further comprising placing the planar target with feature points arbitrarily in a measurement area of the structured-light vision sensor, and forming bright light stripes on the planar target by the projection of the structured-light before performing step b.

4. The method according to claim 2, further comprising placing the planar target with feature points arbitrarily in a measurement area of the structured-light vision sensor, and forming bright light stripes on the planar target by the projection of the structured-light before performing step b.

5. The method according to claim 1, wherein acquiring the images of a planar target used to calibrate the sensor's structure parameters in step b further comprises: taking images of the planar target with a camera and correcting distortion of the images of the planar target.

6. The method according to claim 2, wherein acquiring the images of a planar target used to calibrate the sensor's structure parameters in step b further comprises: taking images of the planar target with a camera and correcting distortion of the images of the planar target.

7. The method according to claim 5, wherein acquiring the coordinates in the camera coordinate frame of the stripes projected by structured-light on the planar target of step b further comprises
    b1. extracting coordinates of feature points on the images of the planar target used to calibrate the structure parameters of the sensor;
    b2. solving a transformation between the image plane and the target plane, and the transformation from the target coordinate frame to the coordinate frame of the camera according to the extracted coordinates of the feature points;
    b3. extracting coordinates of the light stripes on the images of the planar target used to calibrate the structure parameters of the sensor, solving the coordinates in the target coordinate frame of the light stripes on the target according to the transformation between the image plane and the target plane, and converting the coordinates in the target coordinate frame into the camera coordinate frame according to the transformation from the target coordinate frame to the camera coordinate frame.

8. The method according to claim 6, wherein acquiring the coordinates in the camera coordinate frame of the stripes projected by structured-light on the planar target of step b further comprises:
    b1. extracting coordinates of feature points on the images of the planar target used to calibrate the structure parameters of the sensor;
    b2. solving a transformation between the image plane and the target plane, and the transformation from the target coordinate frame to the coordinate frame of the camera according to the extracted coordinates of the feature points;
    b3. extracting coordinates of the light stripes on the images of the planar target used to calibrate the structure parameters of the sensor, solving the coordinates in the target coordinate frame of the light stripes on the target according to the transformation between the image plane and the target plane, and converting the coordinates in the target coordinate frame into the camera coordinate frame according to the transformation from the target coordinate frame to the camera coordinate frame.

9. The method according to claim 5, wherein the images of the planar target comprise light stripes and at least four non-collinear feature points.

10. The method according to claim 6, wherein the images of the planar target comprise light stripes and at least four non-collinear feature points.

11. The method according to claim 7, wherein:
the transformation between the image plane and the target plane in step b2 is in the form of a homographic matrix; and
the transformation from the target coordinate frame to the camera coordinate frame is in the form of a rotation matrix and a translation vector.

12. The method according to claim 8, wherein:
the transformation between the image plane and the target plane in step b2 is in the form of a homographic matrix; the transformation from the target coordinate frame to the camera coordinate frame is in the form of a rotation matrix and a translation vector.

13. The method according to claim 7, wherein the coordinates of the feature points acquired in step b1 are coordinates of at least four non-collinear feature points.

14. The method according to claim 8, wherein the coordinates of the feature points acquired in step b1 are coordinates of at least four non-collinear feature points.

15. The method according to claim 1, wherein the structured-light of step c is structured-light of any pattern.

16. The method according to claim 2, wherein the structured-light of step c is structured-light of any pattern.

* * * * *